United States Patent
Duffy et al.

(10) Patent No.: US 10,822,303 B2
(45) Date of Patent: Nov. 3, 2020

(54) PROCESS FOR PREPARING ELECTRON DEFICIENT OLEFIN PRECURSORS

(71) Applicant: Henkel IP & Holding GmbH, Duesseldorf (DE)

(72) Inventors: Cormac Duffy, Dundalk (IE); Marisa Phelan, Roscrea (IE); Barry Burns, Dublin (IE)

(73) Assignee: Henkel IP & Holding GmbH, Duesseldorf (DE)

( * ) Notice: Subject to any disclaimer, the term of this patent is extended or adjusted under 35 U.S.C. 154(b) by 0 days.

(21) Appl. No.: 16/438,531

(22) Filed: Jun. 12, 2019

(65) Prior Publication Data

US 2019/0292140 A1   Sep. 26, 2019

Related U.S. Application Data

(63) Continuation of application No. PCT/EP2017/082357, filed on Dec. 12, 2017.

(30) Foreign Application Priority Data

Dec. 23, 2016   (GB) .................................. 1622093.1

(51) Int. Cl.
```
C07C 253/30    (2006.01)
C07C 255/19    (2006.01)
B01J 27/12     (2006.01)
B01J 23/10     (2006.01)
B01J 23/20     (2006.01)
B01J 21/06     (2006.01)
B01J 31/22     (2006.01)
```
(52) U.S. Cl.
CPC ............ *C07C 253/30* (2013.01); *B01J 21/066* (2013.01); *B01J 23/10* (2013.01); *B01J 23/20* (2013.01); *B01J 27/12* (2013.01); *B01J 31/2256* (2013.01); *B01J 2231/49* (2013.01); *B01J 2531/38* (2013.01)

(58) Field of Classification Search
CPC ...... C07C 253/30; C07C 255/19; B01J 27/12; B01J 23/10; B01J 23/20; B01J 21/06
See application file for complete search history.

(56) References Cited

U.S. PATENT DOCUMENTS

| | | | |
|---|---|---|---|
| 2,756,251 A | 7/1956 | Joyner et al. | |
| 2,763,677 A | 9/1956 | Jeremias | |
| 3,142,698 A | 7/1964 | Halpern et al. | |
| 3,654,340 A | 4/1972 | Banitt | |
| 3,728,375 A | 4/1973 | Coover, Jr. et al. | |
| 3,903,055 A | 9/1975 | Buck | |
| 3,975,422 A | 8/1976 | Buck | |
| 4,003,942 A | 1/1977 | Buck | |
| 4,012,402 A | 3/1977 | Buck | |
| 4,013,703 A | 3/1977 | Buck | |
| 4,202,920 A | 5/1980 | Renner et al. | |
| 4,364,876 A | 12/1982 | Kimura et al. | |
| 4,512,357 A | 4/1985 | Earl | |
| 4,587,059 A | 5/1986 | Harth et al. | |
| 5,386,047 A | 1/1995 | Nakos et al. | |
| 2,721,858 A | 10/1995 | Joyner et al. | |
| 5,455,369 A | 10/1995 | Meier et al. | |
| 5,624,699 A | 4/1997 | Lang | |
| 5,703,267 A | 12/1997 | Takahashi et al. | |
| 6,096,848 A | 8/2000 | Gololobov et al. | |
| 6,245,933 B1 | 6/2001 | Malofsky et al. | |
| 6,436,866 B1 | 8/2002 | Nishikido et al. | |
| 7,569,719 B1 | 8/2009 | McArdle et al. | |
| 7,659,423 B1 | 2/2010 | McArdle | |
| 7,718,821 B1 | 5/2010 | Bigi et al. | |
| 8,022,251 B2 | 9/2011 | McArdle et al. | |
| 8,053,589 B1 | 11/2011 | McArdle et al. | |
| 8,329,936 B2 | 12/2012 | Friese et al. | |
| 8,481,755 B2 | 7/2013 | McArdle et al. | |
| 8,686,105 B2 | 4/2014 | McArdle et al. | |
| 2012/0023021 A1 | 1/2012 | Seifert et al. | |

FOREIGN PATENT DOCUMENTS

| | | |
|---|---|---|
| CN | 103922964 A | 7/2014 |
| DE | 2738285 A1 | 3/1979 |
| EP | 0459617 A1 | 12/1991 |
| JP | 2012106982 A | 6/2012 |
| WO | 2015004566 A2 | 1/2015 |
| WO | 2015150882 A1 | 10/2015 |

OTHER PUBLICATIONS

Ilangovan, A.; Muralidharan, S. and Maruthamuthu, S. "A Systematic Study on Knoevenagel Reaction and Nazarov Cyclization of Less Reactive Carbonyl Compounds Using Rare Earth Triflates and Its Applications." Journal of the Korean Chemical Society, vol. 55, No. 6, 2011.

Wen-Bun, Y. et al. "Ytterbium Perfluorooctanesulfonate-Catalyzed Knoevenagel Condensation in Fluorous Biphasic System", Organic Preparations and Procedures International, vol. 39, No. 1, 2007, pp. 71-75.

Narsaiah, A. et al. "An Efficient Knoevenagel Condensation Catalyzed by LaCl3. H2O in Heterogenous Medium." Synthetic communications, vol. 33, No. 21, 2003, pp. 3825-3832.

Remme, N. et al. "Scandium Triflate Catalyzed Transesterification of Carboxylic Esters", Synlett, vol. 20007, No. 3, 2007, pp. 491-493.

Fu, X. et al. "Transesterification catalyzed by samarium tri-2-propoxide", Chinese Journal of Chemistry, vol. 15, No. 1, 1997, pp. 90-93.

Vijayalakshmi, V. et al. "Alkyl and substituted alkyl 2-cyanoacrylates. Part 1. Synthesis and properities" J. Adhesion Sci. Technol., vol. 4, No. 9, 1990, pp. 733-750.

Guseva, T. I. et al. "Organic Chemistry: Synthesis of functionally substituted cyanoacetates" Russian Chemical Bulletin, vol. 42, No. 3, Mar. 1993, pp. 478-480.

(Continued)

*Primary Examiner* — Sun Jae Yoo
(74) *Attorney, Agent, or Firm* — Steven C. Bauman

(57) ABSTRACT

This invention relates to a process for producing electron deficient olefin precursors, such as 2-cyanoacetates, using an acid catalyzed transesterification reaction.

7 Claims, 1 Drawing Sheet

(56) References Cited

OTHER PUBLICATIONS

Guseva, T. I. et al. "Organic Chemistry: Synthesis of functionally substituted 2-cyanoacrylates" Russian Chemical Bulletin, vol. 43, No. 4, Apr. 1994, pp. 595-598.

Barrett, A. G. and Braddock, D. C. "Scandium (III) or lanthanide (III) triflates as recyclable catalysts for the direct acetylation of alcohols with acetic acid." Chemical Communications, No. 4, 1997, pp. 351-352.

Gololobov, Y. G. et al. "2-Cyanoacrylates. Synthesis, properties and applications" Russian Chemical Reviews, 66 (11), 1997, pp. 953-962.

Senchenya, N. G. et al. "Silicon-containing esters of α-cyanoacrylic acid: synthesis and properties" Russian Chemical Bulletin, vol. 42, No. 5 May 1993, pp. 909-911.

Renner, A. et al. "Cure of Epoxy Resins with Esters of Cyanoacetic Acid" Journal of Polymer Science: Polymer Chemistry Edition, vol. 23, 1985, pp. 2341-2359.

Buck, Carl J. "Unequivocal Synthesis of Bis(2-Cyannoacrylate) Monomers, I. Via Anthracene Adduets" Journal of Polymer Science, Polymer Chemistry Edition, vol. 16, 1978, pp. 2475-2507.

Leelavathi, P. and Ramesh Kumar, S. "Niobium (V) chloride catalyzed Knoevenagel condensation: An efficient protocol for the preparation of electrophilic alkenes" Journal of Molecular Catalysis A: Chemical 240 (2005) pp. 99-102.

Ogiwara, Y. et al. "Indium(III)-Catalyzed Knoevenagel Condensation of Aldehydes and Activated Methylenes Using Acetic Anhydride as a Promoter" J. Org. Chem., 2015, 80, pp. 3101-3110.

Dawar, P. et al."One-Pot Esterification and Amide Formation via Acid-Catalyzed Dehydration and Ritter Reactions", Synthetic Communications, 2014, 44, pp. 836-846.

Opanasenko, M. "Catalytic behavior of metal-organic frameworks and zeolites: Rationalization and comparative analysis" Catalysis Today, 243, 2015, pp. 2-9.

Bartoli, G. et al. "Highly Efficient Solvent-Free Condensation of Carboxylic Acids with Alcohols Catalysed by Zinc Perchlorate Hexahydrate, Zn(ClO4)2•6H20" Adv. Synth. Catal., 2005, 347, pp. 33-38.

Almasi, M. et al. "Ce(III) and Lu(III) metal-organic frameworks with Lewis acid metalsites: Preparation, sorption properties and catalytic activity inKnoevenagel condensation" Catalysis Today 243, 2015, pp. 184-194.

Viswanadham, B. et al. "The Role of Copper Exchanged Phosphomolybdic Acid Catalyst for Knoevenagel Condensation" Catal. Lett. vol. 146, 2016, pp. 1470-1477.

Cativiela, C. et al. "Synthesis and Preparative Resolution of the trans-Cyclohexane Analogues of Phenylalanine" Eur. J. Org. Chem, 2004, pp. 3898-3908.

Dharma Rao, G. B. and Kaushik, M. P. "Efficient trans-acetoacylation mediated by ytterbium(III) triflate as a catalyst under solvent-free condition." Tetrahedron Letters 52 (2011) pp. 5104-5106.

Lakshmi Kantam, M. et al. "Transesterification of β-keto esters catalyzed by transition metal complexes in a novel heterogeneous way." Catalysis Letters 62 (1999) pp. 67-69.

Magens, S. et al. "A Nucleophilic Fe Catalyst for Transesterifications under Neutral Conditions." Organic Letters, 2008, vol. 10, No. 1, pp. 53-56.

De Sairre, M.I. et al. "Niobium(V) oxide: a new and efficient catalyst for the transesterification of β-keto esters." Tetrahedron Letters 46 (2005) pp. 2705-2708.

Seebach, Dieter. "Diisopropyl (2S,3S)-2,3-O-Isopropylidenetartrate", Organic Syntheses., vol. 65, Jan. 1987, p. 230, XP055445562, ISSN: 0078-6209, DOI: 10.15227/orgsyn.065.0230.

Shantha, K. L. et al. "Developments and applications of cyanoacrylate adhesives." J. Adhesion Sci. Technol. vol., 3, No. 4, 1989, pp. 237-260.

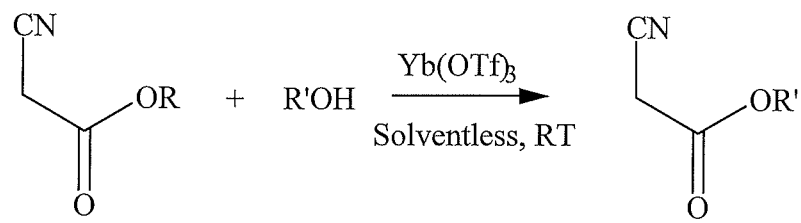

PROCESS FOR PREPARING ELECTRON DEFICIENT OLEFIN PRECURSORS

BACKGROUND

Field

This invention relates to a process for preparing electron deficient olefin precursors, such as 2-cyanoacetates, using an acid catalyzed transesterification reaction.

Brief Description of Related Technology

Cyanoacrylate adhesives are known for their fast adhesion and ability to bond a wide variety of substrates. They are marketed as "super glue" type adhesives. They are useful as an all-purpose adhesive since they are a single component adhesive, very economical as only a small amount will do, and generally do not require any equipment to effectuate curing.

Traditionally, cyanoacrylate monomers have been produced by way of a Knoevenagel condensation reaction between a formaldehyde precursor, such as paraformaldehyde, and an alkyl cyanoacetate with a basic catalyst. During the reaction, cyanoacrylate monomer forms and polymerises in situ to a prepolymer. The prepolymer is subsequently thermally cracked or depolymerised, yielding cyanoacrylate monomer. This approach has remained essentially the same over time, though various improvements and variants have been introduced. See e.g. U.S. Pat. Nos. 6,245,933, 5,624,699, 4,364,876, 2,721,858, 2,763,677 and 2,756,251.

U.S. Pat. No. 5,455,369 defines an improvement in a process for preparing methyl cyanoacrylate, in which methyl cyanoacetate is reacted with formaldehyde to form a polymer that is then depolymerized to the monomeric product, and in which the purity of yield is 96% or better. The improvement of the '369 patent is reported to be conducting the process in a poly(ethylene glycol) diacetate, dipropionate, or dibutyrate, having a number average molecular weight of 200-400, as the solvent.

U.S. Pat. No. 6,096,848 defines a process for the production of a biscyanoacrylate, which comprises the steps of esterifying a 2-cyanoacrylic acid or transesterifying an alkyl ester thereof to obtain a reaction mixture; and fractionally crystallizing the reaction mixture to obtain the biscyanoacrylate.

Recently, a series of U.S. patents have been granted that describe and claim the use of ionic liquids and/or iminium salts in an alternative synthesis of electron deficient olefins. See e.g. U.S. Pat. Nos. 7,659,423; 7,718,821; 7,569,719; 8,022,251; 8,053,589; and 8,686,105.

Nonetheless, commercial production of cyanoacrylate monomers ordinarily relies on the depolymerisation of a prepolymer formed under base-catalyzed Knoevenagel condensation reaction conditions, as noted above. Still today the Knoevenagel condensation reaction is believed to remain the most efficient and prevalent commercial method for producing high yields of monofunctional cyanoacrylates.

It would be advantageous to not have to resort to thermally induced depolymerisation of a prepolymer produced by the Knoevenagel condensation reaction.

Vijayalakshmi et al., *J. Ad. Sci. Technol.*, 4, 9, 733 (1990) describes some approaches to the synthesis of cyanoacetates and corresponding cyanoacrylates, including preparation from chloroacetic acid and its esters by subsequent reaction with sodium cyanide.

Guseva et al., *Russian Chem. Bull.*, 42, 3, 478 (1993) describes functionalized cyanoacetates, many of which were used in the subsequent synthesis of corresponding cyanoacrylates. [See also Guseva et al., *Russian Chem. Bull.*, 43, 4, 595 (1994), and Golobolov and Gruber, *Russian Chem. Rev.*, 66, 11, 953 (1997).]

One of the functionalized cyanoacetates noted in the preceding paragraph is glycidyl cyanoacetate. While the synthesis and characterisation of glycidyl cyanoacetate has been reported, the synthesis, characterisation and provision of performance characteristics of the corresponding glycidyl cyanoacrylate monomer have not to date been published. One explanation for this is that glycidyl cyanoacetate would not survive the conditions of a Knoevenagel reaction to make a cyanoacrylate monomer (initial base catalysis then subsequent exposure to high temperature in presence of strong acids) since epoxides are ring opened under such conditions. And while alternative routes to the glycidyl cyanoacrylate monomer may be conceivable, they would not employ glycidyl cyanoacetate at the outset.

Certain novel compounds having activated methylene groups, including cyanoacetate hybrid molecules, are described and claimed in U.S. Pat. No. 8,481,755.

Other cyanoacetates have been described, such as those with siliconised functionalities. See e.g. Senchenya et al., *Russian Chem. Bull.*, 42, 5, 909 (1993) and European Patent Document No. EP 0 459 617.

And U.S. Pat. No. 8,329,936 (Friese) is directed to and claims a method for producing at least one cyanoacrylic acid ester, comprising the following steps: a) transesterification of at least one 2-cyanoacrylic acid ester of a certain formula, with at least one alcohol of a certain formula, in the presence of at least one transition metal catalyst that is formed by reacting at least one hydroxyl group-containing support material with at least one transition metal alkoxide, and b) isolation of the cyanoacrylic acid ester obtained in step a).

The preparation of mono-, di-, tri- and tetra-functional cyanoacetates, albeit as curatives for epoxy resins for adhesive applications, has been described. Renner et al., "Cure of Epoxy Resins with Esters of Cyanoacrylic Acid", *J. Polym. Sci., Polym. Chem. Ed.*, 23, 2341 (1985) and U.S. Pat. Nos. 4,202,920 and 4,512,357.

Absent from the published literature is the use of transition metal halide- or lanthanide element-containing acid catalysts for transesterification reactions in the preparation of 2-cyanoacetates, or other electron deficient olefin precursors for that matter. Until now.

SUMMARY

By employing a catalyst as described herein in the transesterification reaction, high yields of electron deficient olefin precursors may be realized. These electron deficient olefin precursors once formed may then be used to synthesize electron deficient olefins.

The process for the preparation of a reactive electron deficient olefin precursor is provided herein. In one, more focused, aspect, the invention includes the steps of:

(a) reacting an ester of cyanoacetic acid and an alcohol, in the presence of a catalyst comprising a lanthanide element or a transition metal halide, under appropriate conditions and for a time sufficient to yield a cyanoacetate;

(b) optionally, separating the so-formed cyanoacetate substantially free from the ester of cyanoacetic acid, the alcohol, and/or catalyst, and by-products.

In another, more broad, aspect, the invention provides a process for the preparation of a reactive electron deficient olefin precursor that includes the steps of:
(a) reacting:
(i) a 2-electron withdrawing group-substituted methylene compound embraced by:

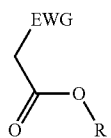

where EWG represents an electron withdrawing group; and R here represents straight chain, branched, cyclic or fused $C_{1-20}$ alkyl, $C_{2-20}$ alkenyl, $C_{2-20}$ alkynyl, and $C_{6-20}$ aryl or $C_{7-20}$ alkaryl, with or without substitution or interruption by one or more heteroatoms; and
(ii) an alcohol, in the presence of a catalyst comprising a lanthanide element or a transition metal halide, under appropriate conditions and for a time sufficient to yield an electron deficient olefin precursor embraced by:

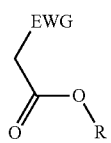

where EWG represents an electron withdrawing group; and R here represents straight chain, branched, cyclic or fused $C_{1-20}$ alkyl, $C_{2-20}$ alkenyl, $C_{2-20}$ alkynyl, and $C_{6-20}$ aryl or $C_{7-20}$ alkaryl, with or without substitution or interruption by one or more heteroatoms, provided that it is different from R in step (a)(i);
(b) optionally, separating so-formed electron deficient olefin precursor substantially free from the 2-electron withdrawing group-substituted methylene compound, the alcohol, the catalyst, and by-products.

BRIEF DESCRIPTION OF THE FIGURE

FIG. 1 depicts a synthetic scheme according to the present invention. More specifically, FIG. 1 shows the reaction of an ester of cyanoacetic acid with an alcohol at ambient temperature in the presence of ytterbium trifluoromethane sulfonate [Yb(OTf)$_3$]. The reaction generates the target 2-cyanoacetate. In the FIGURE, R in the alcohol and the cyanoacetate each represents straight chain, branched, cyclic or fused $C_{1-20}$ alkyl, $C_{2-20}$ alkenyl, $C_{2-20}$ alkynyl, and $C_{6-20}$ aryl or $C_{7-20}$ alkaryl, with or without substitution or interruption by one or more heteroatoms, however they are not the same.

DETAILED DESCRIPTION

As noted above, the present invention provides a process for the preparation of a reactive electron deficient olefin precursor. The process for the preparation of a reactive electron deficient olefin precursor is provided herein. In one, more focused, aspect, the invention includes the steps of:
(a) reacting an ester of cyanoacetic acid and an alcohol in the presence of a catalyst comprising a lanthanide element or a transition metal halide, under appropriate conditions and for a time sufficient to yield a cyanoacetate;
(b) optionally, separating so-formed cyanoacetate substantially free from the ester of cyanoacetic acid, the alcohol, and/or catalyst, and by-products.

In another, more broad, aspect, the invention provides a process for the preparation of a reactive electron deficient olefin precursor that includes the steps of:
(a) reacting:
(i) a 2-electron withdrawing group-substituted methylene compound embraced by:

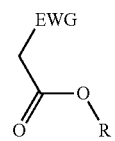

where EWG represents an electron withdrawing group; and R here represents chain, branched, cyclic or fused $C_{1-20}$ alkyl, $C_{2-20}$ alkenyl, $C_{2-20}$ alkynyl, and $C_{6-20}$ aryl or $C_{7-20}$ alkaryl, with or without substitution or interruption by one or more heteroatoms; and
(ii) an alcohol, in the presence of a catalyst comprising a lanthanide element or a transition metal halide, under appropriate conditions and for a time sufficient to yield an electron deficient olefin precursor embraced by:

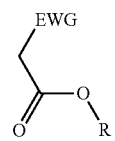

where EWG represents an electron withdrawing group; and R here represents straight chain, branched, cyclic or fused $C_{1-20}$ alkyl, $C_{2-20}$ alkenyl, $C_{2-20}$ alkynyl, and $C_{6-20}$ aryl or $C_{7-20}$ alkaryl, with or without substitution or interruption by one or more heteroatoms, provided it is different from R in step (a)(i);
(b) optionally, separating the so-formed electron deficient olefin precursor substantially free from the 2-electron withdrawing group-substituted methylene compound, the alcohol, and/or the catalyst, and by-products.

By the processes of the present invention yields of electron deficient olefin precursors may be greater than 70%, desirably 80% and more desirably 90%.

In the more broad aspect noted above, the electron deficient olefin precursor so-formed is embraced by:

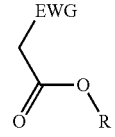

where EWG represents an electron withdrawing group, such as cyano or nitrile, alkoxy or aryloxy (which may itself be substituted by an EWG in the ortho and/or para position on the aromatic ring), carboxyl (e.g., carboxylic acids or carboxylic esters), sulphonic acids, carbonyls, halogens (e.g., F, Cl, Br, and I), nitro, isocyanate, sulfoxide and phosphine oxide; and R here represents straight chain, branched, cyclic or fused $C_{1-20}$ alkyl, $C_{2-20}$ alkenyl, $C_{2-20}$ alkynyl, and $C_{6-20}$ aryl, or $C_{7-20}$ alkaryl, with or without substitution or interruption by one or more heteroatoms.

Reference to FIG. 1 may be useful to appreciate further the present invention, which is described in more detail below and in the Examples section that follows.

As an initial reactant in the inventive processes is the so-described ester of the 2-electron withdrawing group-substituted carboxylic acid. Representative examples of the ester of the 2-electron withdrawing group-substituted carboxylic acid used as a reactant include malonic acid, glycolic acid, an alkyl (e.g., ethyl) nitroacetic acid, an alkyl (e.g., ethyl) haloacetic (like bromoacetic, chloroacetic, and iodoacetic), and cyanoacetic acid, some of which are commercially available for instance from Aldrich Chemical Co. A particularly desirable example of the ester of the 2-electron withdrawing group-substituted carboxylic acid is an ester of cyanoacetic acid.

The amount of the ester of the 2-electron withdrawing group-substituted carboxylic acid that should be used in the inventive process is in the range of about 0.5 to about 2 equivalents, such as about 0.8 equivalents.

Together with the ester of the 2-electron withdrawing group-substituted carboxylic acid as an initial reactant in the inventive processes is an alcohol.

The alcohol may be any mono-, di- or multi-functional hydroxyl compound. Mono-, di- or multi-functional $C_{1-20}$ alkanols, $C_{2-20}$ alkenols, and $C_{2-20}$ alkynols, whether straight chain, branched, cyclic or fused, may be used. Aromatic alcohols, such as phenol, benzyl alcohol and derivatives thereof, may be used.

The alcohol should be used in an amount of about 0.5 to about 2 equivalents, such as about 0.8 equivalents.

The alcohol and the compound should be used in a molar ratio of about 0.5 to about 2 equivalents, such as about 0.8 equivalents.

As noted, the catalyst is one that comprises a lanthanide element or a transition metal halide. The catalyst is acidic in nature, as measured or determined by its ability to donate a hydrogen (proton or hydrogen ion, $H^+$), or, alternatively, its ability to form a covalent bond with an electron pair.

To the lanthanide element or the transition metal halide is bonded, coordinated or complexed, as appropriate, one or more ligands. The ligands may be selected for instance from conventional leaving groups used in organic synthetic schemes. Halogens, tosylates, mesylates, nitrates, and triflates are chief among ligands that are suitable for use herein.

A prime example of a lanthanide element suitable for use in this connection is ytterbium, though others may also be useful, such as lanthanum, cerium, samarium, europium, and dysprosium. Prime examples of a transition metal halide suitable for use in this connection is niobium, zirconium or scandium, with niobium being particularly desirable in this regard.

Desirable catalysts for use in the inventive process include ytterbium trifluoromethane sulfonate [Yb(OTf)$_3$] and niobium halides, such as niobium chloride.

The catalyst should be used in an amount of up to about 20 mol %, such as about 10 mol %.

The electron deficient olefin precursor so formed by the inventive processes may be a variety of olefins having an electron withdrawing group attached to a carbon atom that is alpha to the carbonyl of a carboxylic acid ester.

Representative examples of these electron deficient olefin precursors include esters of malonic acid, esters of glycolic acid, esters of nitroacetic acid (such as ethyl nitroacetate), esters of haloacetic acids (such as ethyl haloacetate—like bromoacetates, chloroacetates, and iodoacetates), and esters of cyanoacetic acid (such as cyanoacetates), some of which are commercially available for instance from Aldrich Chemical Co.

In a desirable embodiment, the reactive electron deficient olefin precursor so formed will be a 2-cyanoacetate.

Representative examples of 2-cyanoacetates so formed by the inventive processes include those having ester groups of methyl, ethyl, propyl, isoamyl, propargyl, butyl, pentyl, hexyl, octyl, nonyl, oxononyl, decyl, dodecyl, allyl, ethynyl, butenyl, cyclohexyl, phenyl, phenethyl, tetrahydrofurfuryl, chloroethyl, 2,2,2-trifluoroethyl, hexafluoroisopropyl, methoxymethyl, methoxyethyl, thiomethoxyethyl, methoxybutyl, thiomethoxybutyl, ethoxyethyl, thioethoxyethyl, propoxyethyl, thioproxyethyl, butoxymethyl, thiobutoxymethyl, butoxyethyl, thiobutoxyethyl and dimethyl siloxane esters of 2-cyanoacetate. This recitation is by no means however exhaustive.

While no solvent is ordinarily needed, the reaction of the inventive processes may proceed in solvent either forming a solution or a suspension. Solvents that may be used include acetonitrile, benzonitrile, chlorobenzene, nitromethane, tetrachloroethene, toluene, THF, 1,4-dioxane, and (poly)ethylene glycol dialkyl ethers or esters, and of course combinations thereof. Ionic liquids may also be used as a solvent. The reaction of the inventive processes may proceed with or without heating or cooling, depending of course on the specific reactants and the scale of the reaction.

While the reaction ordinarily occurs at ambient temperature, gentle heating up to a temperature of 70° C. may be applied. The temperature may be reached through an external heating element or internally by means of the exotherm that may be generated depending on the identity of the reactants. The temperature of the reaction should be controlled however to accommodate any such exothermic processes.

The time of reaction may be monitored by reference to the formation of the desired electron deficient olefin precursor product. $^1$H NMR spectrometer is a particularly useful tool in this regard. The time of reaction may be as little as 30 minutes, for instance, or longer or shorter for that matter depending again on the identity of the specific reactants, the scale of the reaction and whether heat is added to the reaction conditions.

Once formed, the electron deficient olefin precursor may be isolated as a product or may be used directly in situ to form an electron deficient olefin. The in situ use would be for instance as a reactant in a Knoevenagel condensation reaction with an aldehyde source conducted under conventional base catalyzed conditions or under state of the art acid catalyzed conditions.

The following examples are intended to illustrate but in no way limit the present invention.

EXAMPLES

Example 1

To a 25 ml round bottomed flask is added 7.01 g (0.062 mol) of ethyl cyanoacetate, 4.15 g (0.056 mol) of n-butanol and 10 mL of nitromethane. The flask is fitted with a reflux condenser and magnetic stirrer before being immersed in an oil bath at a temperature of 105° C. The mixture is stirred at this temperature for a period of time of 30 minutes before a mixture of 3.47 g (6.75 mmol, 10 mol %) of ytterbium triflate in 5 ml of acetonitrile is added. The reaction is stopped after a period of time of 6 hours. The conversion to butyl cyanoacetate is determined by 500 MHz $^1$H NMR.

Example 2

To a 25 ml round bottomed flask is added 7.01 g (0.062 mol) of ethyl cyanoacetate, 4.936 g (0.056 mol) of 2-pentanol and 10 mL of nitromethane. The flask is fitted with a reflux condenser and magnetic stirrer before being immersed in an oil bath at a temperature of 105° C. The mixture is stirred at this temperature for a period of time of 30 minutes before a mixture of 3.47 g (6.75 mmol, 10 mol %) of ytterbium triflate in 5 ml of acetonitrile is added. The reaction is stopped after a period of time of 6 hours. The conversion to 2-pentyl cyanoacetate is determined by 500 MHz $^1$H NMR.

Example 3

To a 25 ml round bottomed flask is added 7.01 g (0.062 mol) of ethyl cyanoacetate, 6.84 g (0.056 mol) of phenyl ethanol and 10 mL of nitromethane. The flask is fitted with a reflux condenser and magnetic stirrer before being immersed in an oil bath at a temperature of 105° C. The mixture is stirred at this temperature for a period of time of 30 minutes before a mixture of 3.47 g (6.75 mmol, 10 mol %) of ytterbium triflate in 5 ml of acetonitrile is added. The reaction is stopped after a period of time of 6 hours. The conversion to phenyl ethyl cyanoacetate is determined by 500 MHz $^1$H NMR.

What is claimed is:

1. A process for the preparation of a cyanoacetate, steps of which comprise:
    (a) reacting an ester of cyanoacetic acid and an alcohol, in the presence of a catalyst comprising a lanthanide element, wherein the lanthanide element comprises ytterbium, under appropriate conditions and for a time sufficient to yield a cyanoacetate;
    wherein the alcohol is present in an amount of from about 0.5 to about 2.0 equivalents relative to the ester of the cyanoacetic acid; and wherein the catalyst is present in an amount of up to about 20 mol %;
    (b) optionally, separating the so-formed cyanoacetate from the reaction mixture to be substantially free from the ester of cyanoacetic acid the alcohol and/or the catalyst, and by-products.

2. The process of claim 1, wherein the catalyst comprising a lanthanide element has one or more ligands bound to the element(s).

3. The process of claim 2, wherein the one or more ligands is selected from halogens, triflates, mesylates, nitrates or tosylates.

4. The process of claim 1, wherein the alcohol is any mono-, di- or multi-functional hydroxyl compound.

5. The process of claim 1, wherein the alcohol is any mono-, di- or multi-functional $C_{1-20}$ alkanol, $C_{2-20}$ alkenol, or $C_{2-20}$ alkynol.

6. The process of claim 1, wherein the alcohol is an aromatic alcohol.

7. The process of claim 1, wherein the alcohol is phenol, benzyl alcohol or derivatives thereof.

* * * * *